(12) United States Patent
Chen (10) Patent No.: US 9,937,082 B2
(45) Date of Patent: Apr. 10, 2018

(54) WETNESS NOTIFICATION SYSTEM (71) Applicant: I-Ding Medical Equipment Co., Ltd., Kaohsiung (TW)

(72) Inventor: Hung Chi Chen, Kaohsiung (TW)

(*) Notice: Subject to any disclaimer, the term of this patent is extended or adjusted under 35 U.S.C. 154(b) by 52 days.

(21) Appl. No.: 15/073,863

(22) Filed: Mar. 18, 2016

(65) Prior Publication Data
US 2016/0278990 A1    Sep. 29, 2016

(30) Foreign Application Priority Data

Mar. 26, 2015  (TW) .............. 104204574 U (51) Int. Cl.
| | |
|---|---|
| A61F 13/42 | (2006.01) |
| G08B 21/20 | (2006.01) |
| G08B 21/04 | (2006.01) |
| G08B 25/08 | (2006.01) |
| A61B 5/00 | (2006.01) |
| A61F 5/44 | (2006.01) |
| A61L 15/56 | (2006.01) |
| G08B 21/02 | (2006.01) |

(52) U.S. Cl.
CPC .......... A61F 13/42 (2013.01); A61B 5/6808 (2013.01); G08B 21/0461 (2013.01); G08B 21/20 (2013.01); G08B 25/08 (2013.01); A61B 5/6801 (2013.01); A61F 5/4404 (2013.01); A61F 2013/424 (2013.01); A61L 15/56 (2013.01); G08B 21/0288 (2013.01)

(58) Field of Classification Search
CPC ............ A61F 13/42; A61F 2013/424; A61F 2013/425; A61F 2013/422; A61F 5/4404; A61L 15/56; A61B 5/6808; A61B 5/6804; A61B 5/0002; A61B 5/6801; A61B 5/6802; G08B 21/20; G08B 21/0461; G08B 21/0288; G08B 21/18; G08B 25/10
USPC .................. 604/361; 340/604, 605, 603
See application file for complete search history.

(56) References Cited

U.S. PATENT DOCUMENTS

| | | | |
|---|---|---|---|
| 7,315,242 B2* | 1/2008 | Eisenman | B60R 25/1003 340/426.1 |
| 2004/0207530 A1 | 10/2004 | Nielsen | |
| 2007/0024457 A1 | 2/2007 | Long et al. | |
| 2014/0198203 A1* | 7/2014 | Vardi | G08B 21/20 348/135 |

FOREIGN PATENT DOCUMENTS

| | | |
|---|---|---|
| CN | 2013-2172452 | 10/2013 |
| JP | 11-299830 | 2/1999 |
| JP | 2001-027640 | 1/2001 |
| JP | 2012-105839 | 6/2012 |

* cited by examiner

*Primary Examiner* — Benyam Haile
(74) *Attorney, Agent, or Firm* — Pro-TECHTOR International Services; Ian Oglesby (57) ABSTRACT

A wetness notification system includes a detecting unit (2), a clip unit (3), a receiver unit (4), and a sampling unit (5). The detecting unit (2) includes a sleeve body (21), amounting seat (29), a moisture detector (22), a casing (23), a processor (24), a wireless transmitter (25), and a battery (26). The sampling unit (5) includes a substrate (51) and at least one sampling element (52). The substrate (51) is made of flexible material and removably attached to the mounting seat (29). The sampling element (52) is disposed on the substrate (51) for contacting and sampling the urine within the clothing article (7) for urinalysis.

10 Claims, 5 Drawing Sheets

FIG.5

WETNESS NOTIFICATION SYSTEM

CROSS-REFERENCE TO RELATED APPLICATION

This application claims priority of Taiwanese Patent Application No. 104204574, filed on Mar. 26, 2015.

FIELD

The disclosure relates to a notification system, more particularly to a wetness notification system for detecting and notifying wetness in a clothing article.

BACKGROUND

A conventional diaper with a wetness sensing device includes a first non-woven fabric layer, two strip electrodes, a second non-woven fabric layer, a liquid absorbing layer made from a liquid absorbing material, a liquid-proof layer and two metallic sockets. A first side of the first non-woven fabric layer absorbs a liquid excreted from a human body 8, and the liquid permeates to a second side of the first non-woven fabric layer. The strip electrodes are attached onto the second side of the first non-woven fabric layer, and the strip electrodes are electrically connected when they come into contact with the liquid. A first side of the second non-woven fabric layer is attached to the second side of the first non-woven fabric layer and to the strip electrodes, and the strip electrodes are thus retained between the first and second non-woven fabric layers. The first side of the second non-woven fabric layer absorbs the liquid, which permeates to a second side of the second non-woven fabric layer. The liquid absorbing layer is attached to the second side of the second non-woven fabric layer, and absorbs that liquid permeated through the second non-woven fabric layer. The liquid-proof layer is made from a liquid proof material. A first side of the liquid-proof layer is attached to the second side of the liquid absorbing layer, and retains the liquid that permeated through the liquid absorbing layer to prevent the liquid from leaking out of the diaper. Each of the metallic sockets has a first engaging portion that engages with a respective one of two engaging bodies of an electrical detection device. This enables the electrical detection device to detect the electrical conduction between the strip electrodes when a liquid is excreted, and to send a wetness notification signal for notifying a caregiver to change the diaper according to the wetness notification signal.

However, the electrical detection device requires a battery for operation. Due to the absence of a low electricity notification mechanism for notification when the battery is low in electricity, untimely changing of the diaper may lead to skin allergies, rashes and other skin diseases. Moreover, the strip electrodes are sewn into the diaper, and sewing increases labor costs and may cause a rise in defective products.

Thus, a conventional wetness notification system for detecting wetness in a clothing article configured for absorbing urine has been developed to solve the problems mentioned above. However, such conventional system still lacks certain features, such as urine sampling and urinalysis, to provide early diagnosis for certain diseases. For example, by sampling a user's urine and analyzing the concentrations of the substances therein such as proteins, nitrite, glucose, ketones, bilirubin, occult blood, leukocytes, urobilinogen, etc., or analyzing the physical or chemical properties of the sampled urine such as specific gravity, pH value, etc., a more thorough understanding of the user's health status can be achieved.

SUMMARY

Therefore, an object of the disclosure is to provide a wetness notification system that can alleviate at least one of the drawbacks of the prior art.

According to the disclosure, the wetness notification system includes a detecting unit, a clip unit, a receiver unit, and a sampling unit.

The detecting unit includes a sleeve body, amounting seat combined with the sleeve body, a moisture detector mounted on the mounting seat and configured to output a notification signal when a surrounding moisture level detected thereby is greater than a threshold moisture level, a casing, a wireless transmitter disposed in the casing, a processor disposed in the casing, electrically connected to the moisture detector and the wireless transmitter, and configured to receive the notification signal outputted by the moisture detector and to transmit the notification signal through the wireless transmitter, and a battery disposed in the casing and configured to provide electricity to the moisture detector, the processor and the wireless transmitter.

The clip unit includes a first portion removably inserted into the sleeve body, a curved second portion extending from the first portion, and a third portion extending from the curved second portion, removably supporting the casing, and configured to cooperate with the first portion to clip the detecting unit onto the clothing article in a manner that the sleeve body and the mounting seat are disposed at an inner side of the clothing article and the third portion is disposed at an outer side of the clothing article.

The receiver unit includes a wireless receiver configured to communicate wirelessly with the wireless transmitter for receiving the notification signal therefrom, a notifying module, and a controller electrically connected to the wireless receiver and the notifying module and configured to drive the notifying module to output a wetness notification in response to receipt of the notification signal from the wireless receiver.

The sampling unit includes a substrate made of flexible material and removably attached to the mounting seat, and at least one sampling element disposed on the substrate for contacting and sampling urine within the clothing article for urinalysis.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Referring to FIGS. 1 to 4, an exemplary embodiment of a wetness notification system for detecting and notifying wetness in a clothing article 7 according to the present disclosure includes a detecting unit 2, a clip unit 3, a receiver unit 4, a sampling unit 5, and a positioning member 6.

Figure 1:
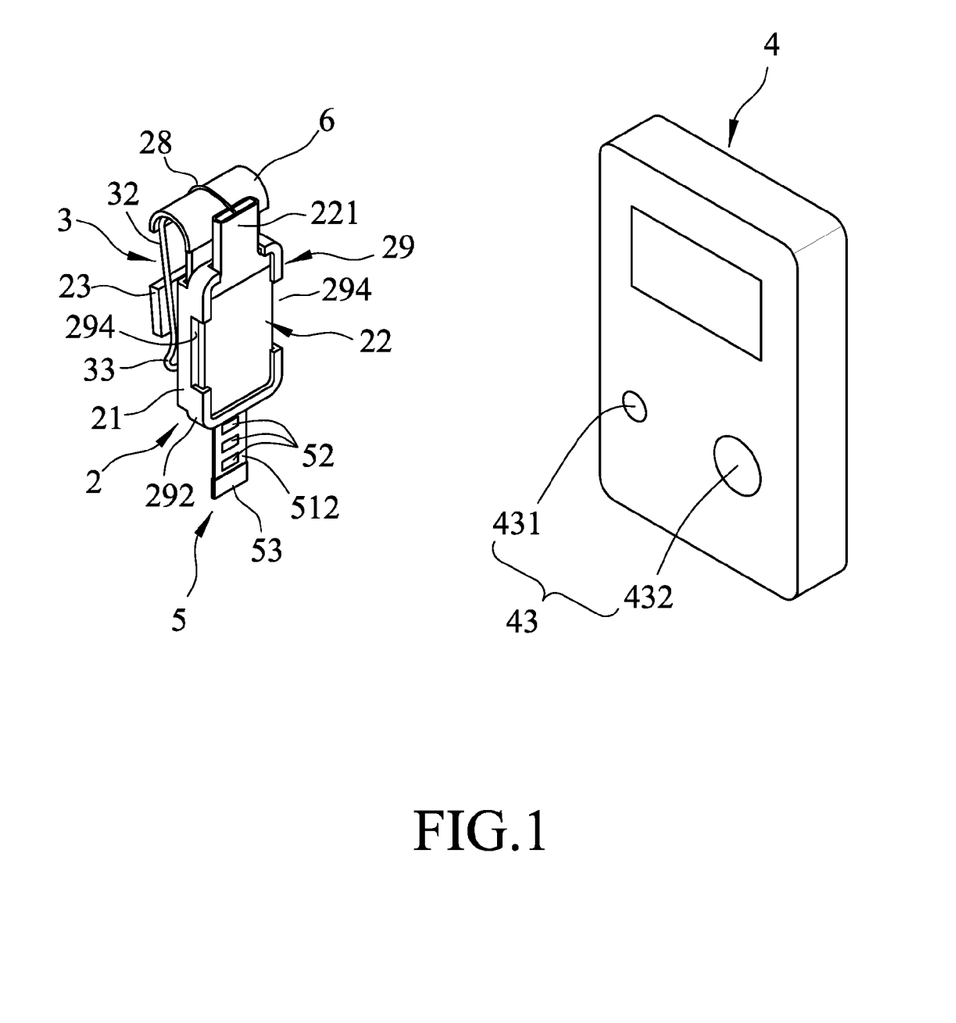
FIG. 1 is a perspective view illustrating an exemplary embodiment of a wetness notification system of the disclosure.
Figure 2:
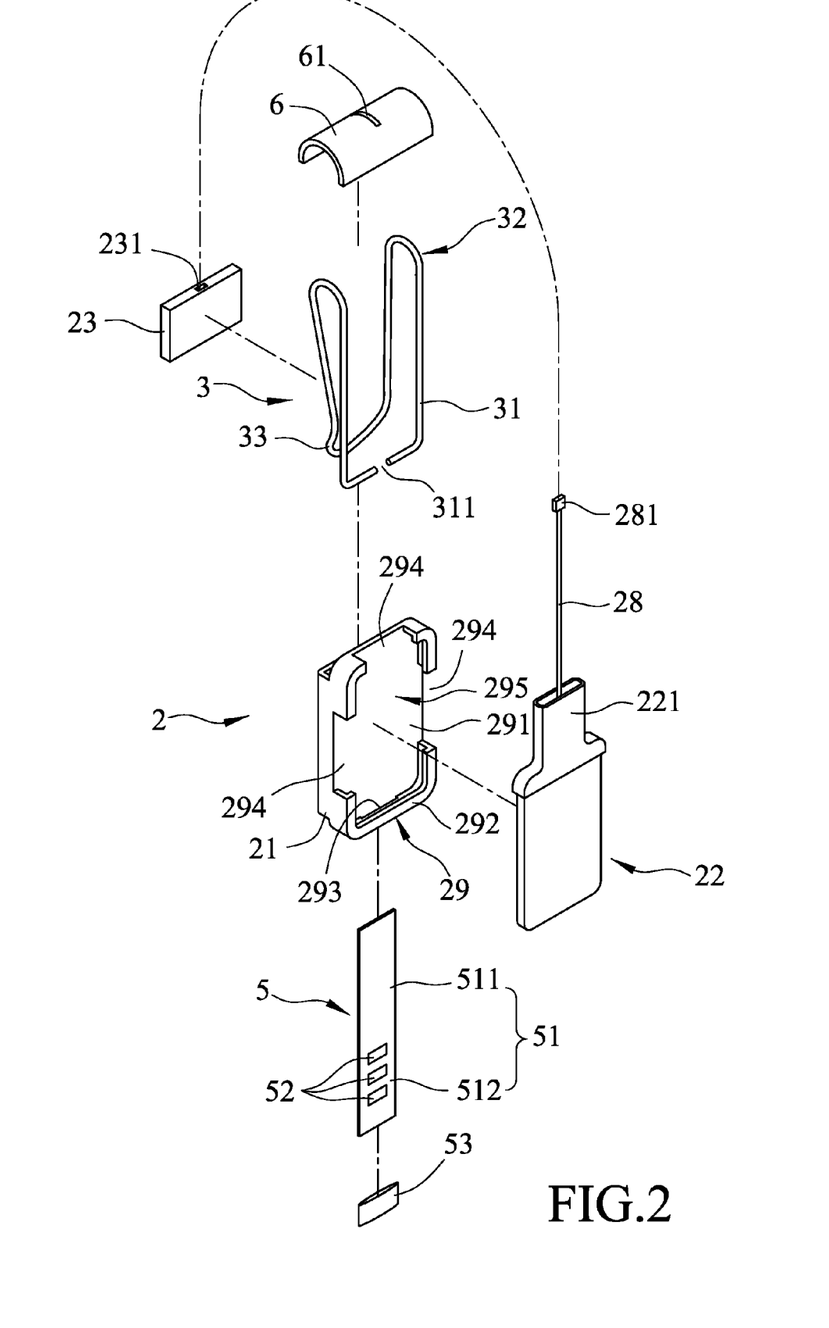
FIG. 2 is an exploded perspective view illustrating a detecting unit and a clip unit of the exemplary embodiment shown in FIG. 1.
Figure 5:
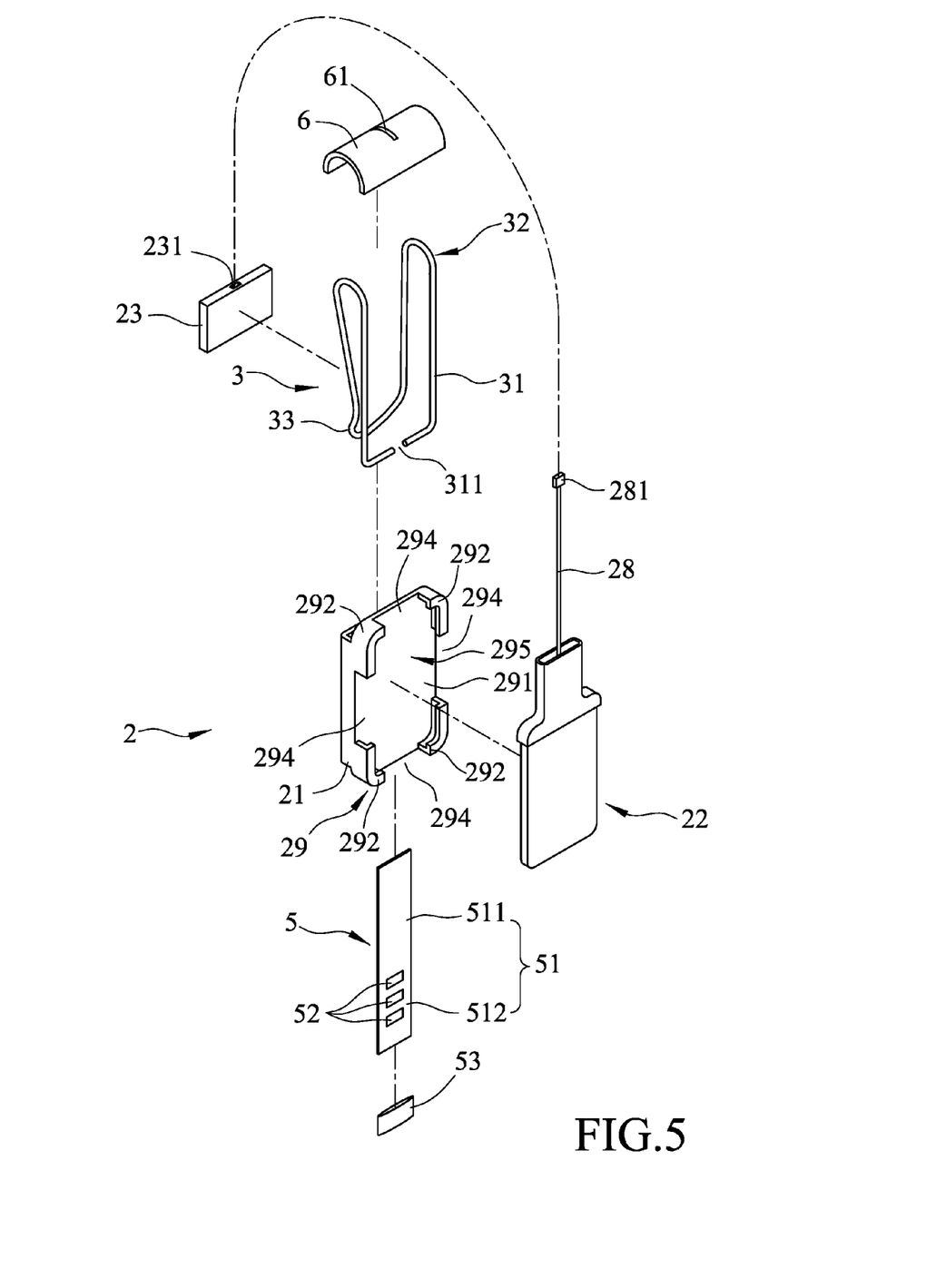
FIG. 5 is an exploded perspective view illustrating a variation of the exemplary embodiment.

The detecting unit 2 includes a sleeve body 21, a mounting seat 29 combined with the sleeve body 21, a moisture detector 22 mounted on the mounting seat 29, a casing 23, a wireless transmitter 25 that is disposed in the casing 23, a processor 24 that is disposed in the casing 23 and that is electrically connected to the moisture detector 22 and the wireless transmitter 25, and a battery 26 that is disposed in the casing 23 and that provides electricity to the processor 24 and the wireless transmitter 25. In this embodiment, the detecting unit 2 further includes an electricity detector 27 that is disposed in the casing 23 and that is electrically connected to the battery 26 and the processor 24 (see FIG. 3), and a transmission wire 28 as illustrated in FIG. 2. As shown in FIG. 2, the mounting seat 29 of this embodiment includes a base plate 291, and a positioning wall 292 that surrounds a periphery of the base plate 291, that cooperates with the base plate 291 to define an accommodating space 295 where the moisture detector 22 is tightly and removably disposed, and that is formed with a through hole 293 and a plurality of notches 294 (three notches are shown in FIG. 2). The notches 294 are depressed toward the base plate 291 and facilitate deformation of the positioning wall 292 for removing the moisture detector 22 from the accommodating space 295. It is worth noting that, in certain embodiments, the positioning wall 292 may be formed with an additional notch instead of being formed with the through hole 293 as illustrated in FIG. 5. In this embodiment, the casing 23 includes an input port 231 as illustrated in FIG. 1. The battery 26 is electrically connected with the moisture detector 22, the wireless transmitter 25 and the electricity detector 27. The transmission wire 28 has a first end that is electrically connected to a connecting portion 221 of the moisture detector 22 which extends through one of the notches 294, and a second end that includes a connector 281 removably inserted into the input port 231 of the casing 23 so as to electrically connect the transmission wire 28 to the processor 24.

The clip unit 3 of this embodiment is a hollow frame made from a bent flexible loop-shaped member as illustrated in FIG. 2, and has a first portion 31 removably inserted into the sleeve body 21, a curved second portion 32 that extends from the first portion 31, and a third portion 33 that extends from the curved second portion 32, that removably supports the casing 23, and that cooperates with the first portion 31 to clip the detecting unit 2 onto the clothing article 7. In this embodiment, the third portion 33 may have an overall width less than that of the first portion 31. The first portion 31 of this embodiment has two separate segments defining a gap 311 therebetween which facilitates deformation of the first portion 31 when the same is being removably inserted into the sleeve body 21.

The receiver unit 4 of this embodiment includes a wireless receiver 41 to communicate wirelessly with the wireless transmitter 25, a notifying module 43, a controller 42 electrically connected to the wireless receiver 41 and the notifying module 43, a timer 44 electrically coupled to the controller 42 and storing a predetermined period value, and an electricity source 45 electrically coupled with the controller 42 to provide electricity to the receiver unit 4. The controller 42 of this embodiment is configured to have a normal notification mode and a looping notification mode, which will be described in greater detail in the following paragraphs. The notifying module 43 may include a light emitting element 431 for emitting light, and a speaker 432 for outputting sound. It is worth noting that, in other embodiments, the timer 44 can be integrated into the controller 42, i.e., the controller 42 is capable of performing a time-counting function. A frequency used for wireless communication between the wireless transmitter 25 and the wireless receiver 41 can be preset in the factory. Alternatively, a tuner (not shown in the Figures) may be incorporated in the wetness notification system for adjusting the frequency in other embodiments of this disclosure.

Figure 4:
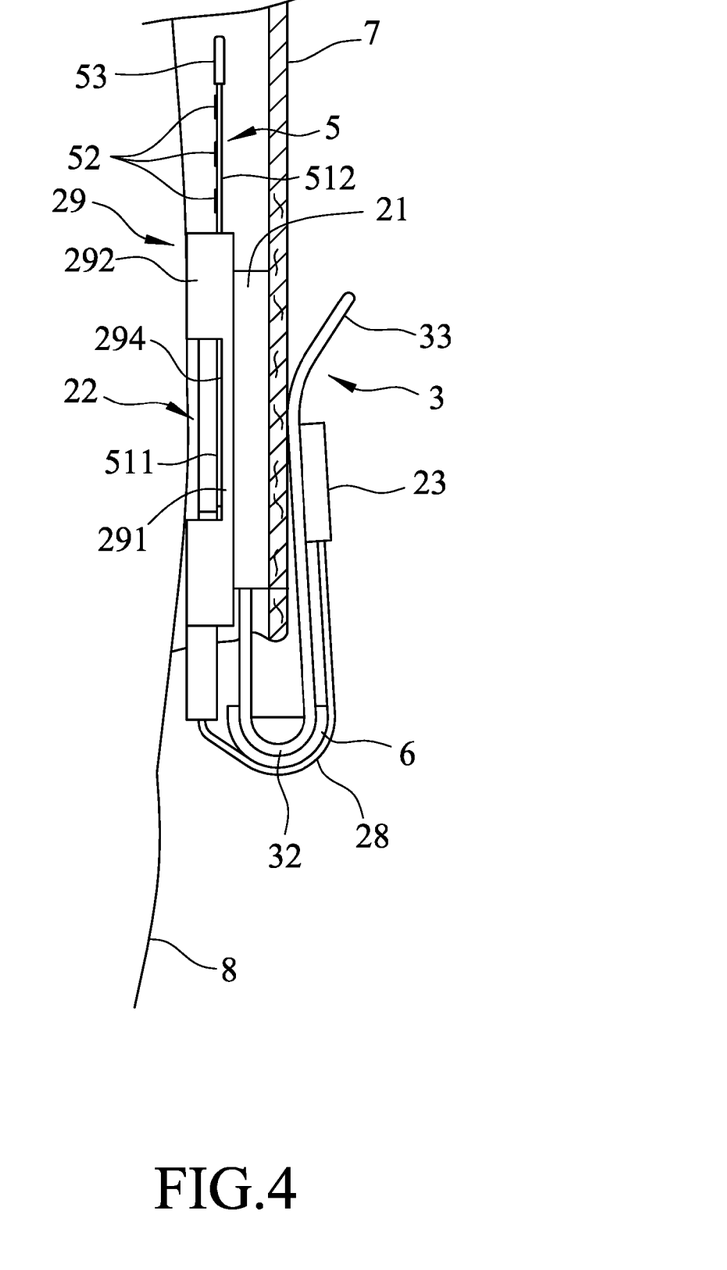
FIG. 4 is a partially sectional view of the exemplary embodiment shown in FIG. 1, illustrating that the wetness notification system is used with a clothing article.

As illustrated in FIG. 2, the sampling unit 5 of this embodiment includes a substrate 51 that is made of a flexible material, such as silicone, and that is removably attached to the mounting seat 29, and a plurality of sampling elements 52 that are disposed on the substrate 51 for contacting and sampling urine within the clothing article 7. It should be noted that each sampling element 52 may be a test paper for simultaneously sampling and testing the urine like in this embodiment, or a vessel for sampling the urine used for subsequent urinalysis in other embodiments of this disclosure. As illustrated in FIGS. 1, 2 and 4, the substrate 51 includes a first segment 511 disposed in the accommodating space 295 and sandwiched in between the moisture detector 22 and the base plate 291, and a second segment 512 extending from the first segment 511 through the positioning wall 292 out of the mounting seat 29 and mounted with the sampling elements 52. In this embodiment, the second segment 512 extends from the first segment 511 through the through hole 293 formed on the positioning wall 292. In the embodiments where the through hole 293 is replaced by the additional notch 294, the second segment 512 may extend through such additional notch 294 as illustrated in FIG. 5. In this embodiment, the sampling unit 5 further includes a protection sleeve 53 that is made of silicone, that covers a distal end of the second segment 512 without covering any of the sampling elements 52, and that has a curved end opposite to the first segment 511 for reducing discomfort of a user when the user is in direct contact therewith.

It is worth noting that the number of the sampling elements 52 included in the wetness notification system is not limited, i.e., to have one single sampling element 52 provided on the second segment 512 may suffice in other embodiments according to the present disclosure. Moreover, the configuration of the sampling elements 52 is not limited herein, for example, each of the sampling elements 52 may be configured into a rectangular shape, a strip, etc. Furthermore, the sampling elements 52 may be removably attached onto the second segment 512 so that the sampling elements 52 may be easily replaced after use.

The positioning member 6 engages the clip unit 3 and is formed with a slit 61 for receiving a section of the transmission wire 28 so as to position the transmission wire 28 as illustrated in FIG. 1.

As shown in FIGS. 1, 2 and 4, the wetness notification system can be applied on the clothing article 7 (such as pad-type or pant-type diapers), which is wearable on a human body 8. When in use, the first portion 31 of the clip unit 3 is inserted into the sleeve body 21, the casing 23 is disposed on the third portion 33 of the clip unit 3, and the transmission wire 28 is positioned by the slit 61 of the positioning member 6 with the connector 281 being plugged into the input port 231 of the casing 23. The sleeve body 21, the moisture detector 22, and the sampling unit 5 are all disposed at an inner side of the clothing article 7, preferably adjacent to the groin area of the human body 8, and the third portion 33 is disposed at an outer side of the clothing article 7. It may be noted that, in this embodiment, the clip unit 3 exhibits light-weight characteristics due to its hollow frame structure, and reduces the burden of the user when the user is carrying the clip unit 3. Moreover, the design of the curved second portion 32 can enhance the comfort of the user. Furthermore, the receiver unit 4 can be carried around by a caregiver or be placed at a specific location that can be seen by the caregiver.

Figure 3:
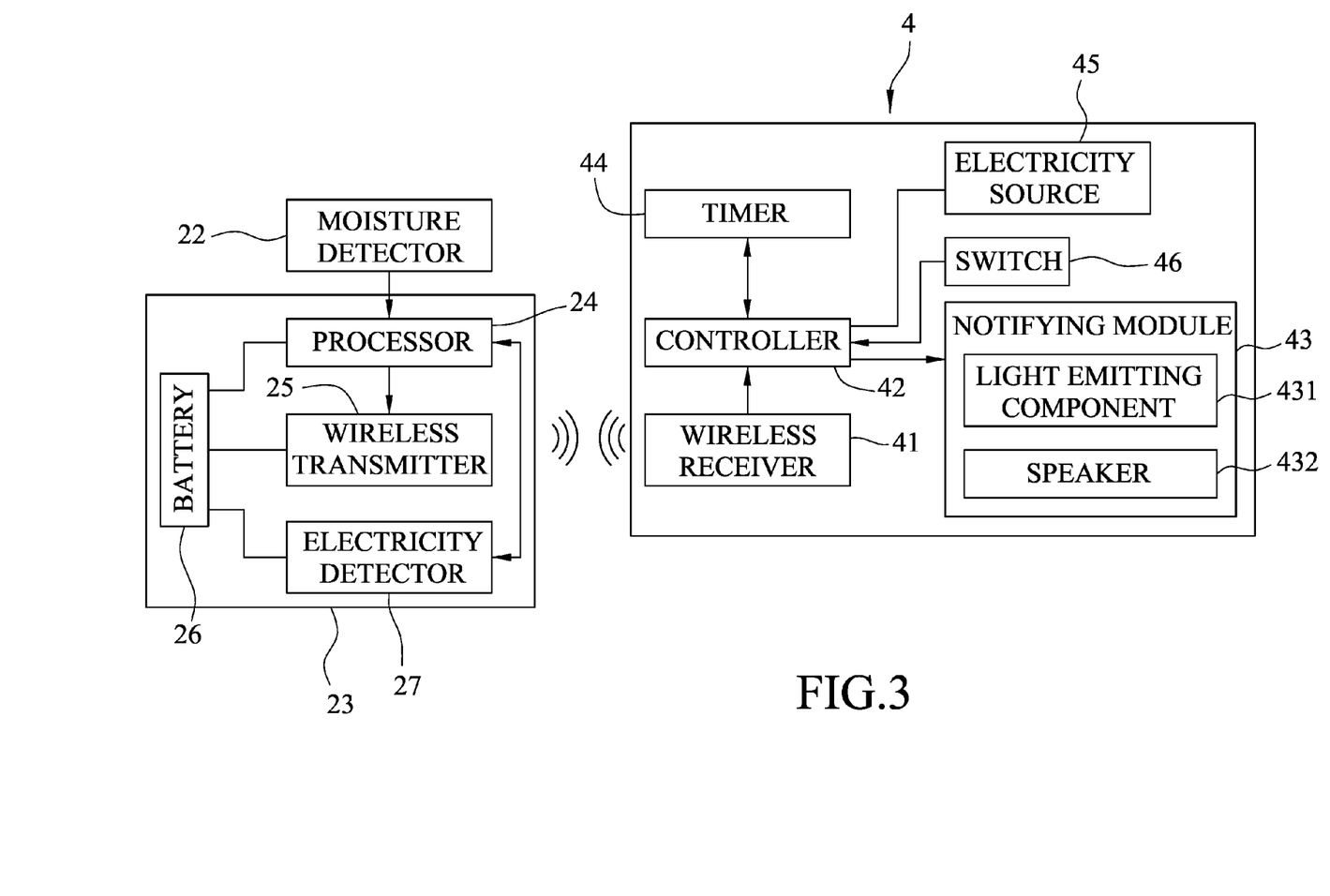
FIG. 3 is a schematic block diagram of the exemplary embodiment shown in FIG. 1.

As shown in FIGS. 3 and 4, the moisture detector 22 is configured to output a notification signal when a surrounding moisture level detected thereby, e.g., the moisture around the groin area, is greater than a threshold moisture level upon the detecting unit 2 being clipped onto the clothing article 7. The processor 24 is configured to receive the notification signal outputted by the moisture detector 22, and to transmit the notification signal through the wireless transmitter 25. The wireless receiver 41 is configured to communicate wirelessly with the wireless transmitter 25 for receiving the notification signal therefrom, and the controller 42 is configured to receive the notification signal through the wireless receiver 41 of the receiver unit 4. When the controller 42 receives the notification signal for a first time via the wireless receiver 41, the controller 42 executes the normal notification mode to drive the notifying module 43 to output a wetness notification in response to receipt of the notification signal, and at the same time configures the timer 44 to start counting. The controller 42 configures the notifying module 43 to stop outputting the wetness notification when the timer 44 has counted to the predetermined period value. The wetness notification may be the light emitted by the light emitting element 431, and/or the sound outputted by the speaker 432, so as to alert the caregiver for replacement of the clothing article 7.

After the notifying module 43 stops outputting the wetness notification, if the controller 42 continues receiving the notification signal via the wireless receiver 41, the controller 42 executes the looping notification mode to configure the notifying module 43 to output the wetness notification intermittently until the controller 42 no longer receives the notification signal. The looping notification mode of the controller 42 helps to remind the caregiver to replace the clothing article 7 so as to prevent rashes and other skin diseases on the user.

Referring to FIGS. 3 and 4, when the clothing article 7 absorbs urine, the sampling elements 52 of the sampling unit 5 simultaneously contact the urine and perform the urine test, thus allowing the caregiver to observe the color on the sampling elements 52 while replacing the clothing article 7, and to compare the color with a color chart to get the results. Therefore, the caregiver can monitor the user's health status in real time and be able to watch for any possible diseases that may affect the user.

In this embodiment, the electricity detector 27 detects the residual electricity of the battery 26. When the residual electricity detected by the electricity detector 27 is lower than a threshold electricity value, the electricity detector 27 is configured to output a low battery signal to the processor 24, which is then configured to transmit the low battery signal through the wireless transmitter 25. When the controller 42 receives the low battery signal for a first time via the wireless receiver 41, the controller 42 executes the normal notification mode to drive the notifying module 43 to output a low electricity notification in response to receipt of the low battery signal, and at the same time configures the timer 44 to start counting.

The controller 42 configures the notifying module 43 to stop outputting the low electricity notification when the timer 44 has counted to the predetermined period value. The low electricity notification may be the light emitted by the light emitting element 431, and/or the sound outputted by the speaker 432. Similarly, after the notifying module 43 stops outputting the low electricity notification, if the controller 42 continues receiving the low battery signal via the wireless receiver 41 (such as when the battery 26 is yet to be replaced), the controller 42 executes the looping notification mode to configure the notifying module 43 to output the low electricity notification intermittently until the controller 42 no longer receives the low battery signal. In the same manner, when the residual electricity in the electricity source 45 is low, the controller 42 configures the notifying module 43 to output the low electricity notification until the electricity in the electricity source 45 is no longer low. The low electricity notification can prevent the caregiver from failing to replace the clothing article 7 when the notification module 43 cannot timely respond to the wetness in the clothing article 7 due to the lack of electricity in the battery 26 or in the electricity source 45.

In this embodiment, the moisture detector 22 and the clip unit 3 are removable from the mounting seat 29. The casing 23 that contains the processor 24, the wireless transmitter 25, the battery 26 and the electricity detector 27 is removable from the clip unit 3. The transmission wire 28 is also removable from the casing 23. Such configurations provide convenience in washing, repair and replacement of individual units in the wetness notification system.

Particularly, the receiver unit 4 further includes a switch 46 electrically coupled with the controller 42. When the controller 42 executes the normal notification mode to configure the notifying module 43 to output one of the wetness notification and the low electricity notification, the controller 42 configures the timer 44 to start counting, and the switch 46 may be operated by the caregiver to control the controller 42 to control in turn the notifying module 43 to stop outputting one of the wetness notification and the low electricity notification. When the timer 44 has counted to the predetermined period value and the controller 42 continues receiving the one of the notification signal and the low battery signal via the wireless receiver 41, the controller 42 executes the looped notification mode to configure the notifying module 43 to output the corresponding one of the wetness notification and the low electricity notification intermittently.

In summary, the inclusion of the sampling unit 5 in the wetness notification system of this disclosure not only allows for urinalysis to be performed immediately such that the caregivers can monitor the user's health status in real time, but can also notify the caregiver when the wetness notification system detects the wetness in the clothing article. Moreover, it is possible to use the urine sampled by the sampling elements 52 for bacterial culture. In addition, it is also possible to replace the sampling elements 52 if necessary. In addition to wetness detection by the moisture detector 22 and the processor 24, the electricity detector 27 detects the residual electricity of both the battery 26 and the electricity source 45, and the notifying module 43 outputs the notification signal (such as light and/or sound) more than once when low residual electricity is detected, such that the caregiver can replace the battery 26 or replenish the electricity in the electricity source 45. In such manner, the caregiver can replace the clothing article 7 to prevent rashes and other skin diseases on a wearer and be notified to keep the wetness notification system working. Moreover, the wetness notification system includes the moisture detector 22 and the clip unit 3 that are removable from the mounting seat 29, the casing 23 that is removable from the clip unit 3, and the transmission wire 28 that is removable from the casing 23, and such removal design provides convenience in washing, repair and replacement of individual units in the wetness notification system.

In the description above, for the purposes of explanation, numerous specific details have been set forth in order to provide a thorough understanding of the embodiment (s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

What is claimed is:

1. A wetness notification system for detecting and notifying wetness in a clothing article (7) that is configured for absorbing urine, the wetness notification system being characterized by:
    a detecting unit (2) that includes
        a sleeve body (21),
        a mounting seat (29) combined with said sleeve body (21),
        a moisture detector (22) mounted on said mounting seat (29), and configured to output a notification signal when a surrounding moisture level detected thereby is greater than a threshold moisture level,
        a casing (23),
        a wireless transmitter (25) disposed in said casing (23),
        a processor (24) disposed in said casing (23), electrically connected to said moisture detector (22) and said wireless transmitter (25), and configured to receive the notification signal outputted by said moisture detector (22) and to transmit the notification signal through said wireless transmitter (25), and
        a battery (26) disposed in said casing (23) and configured to provide electricity to said moisture detector (22), said processor (24) and said wireless transmitter (25);
    a clip unit (3) that includes
        a first portion (31) removably inserted into said sleeve body (21),
        a curved second portion (32) extending from said first portion (31), and
        a third portion (33) extending from said curved second portion (32), removably supporting said casing (23), and configured to cooperate with said first portion (31) to clip said detecting unit (2) onto the clothing article (7) in a manner that said sleeve body (21) and said mounting seat (29) are disposed at an inner side of the clothing article (7) and that said third portion (33) is disposed at an outer side of the clothing article (7);
    a receiver unit (4) that includes a wireless receiver (41) configured to communicate wirelessly with said wireless transmitter (25) for receiving the notification signal therefrom, a notifying module (43), and a controller (42) electrically connected to said wireless receiver (41) and said notifying module (43) and configured to drive said notifying module (43) to output a wetness notification in response to receipt of the notification signal from said wireless receiver (41); and
    a sampling unit (5) that includes a substrate (51) made of flexible material and removably attached to said mounting seat (29), and at least one sampling element (52) disposed on said substrate (51) for contacting and sampling urine within the clothing article (7) for urinalysis,
    wherein said mounting seat (29) includes a base plate (291), and a positioning wall (292) surrounding a periphery of said base plate (291) and cooperating with said base plate (291) to define an accommodating space (295) where said moisture detector (22) is tightly disposed,
        wherein said substrate (51) includes a first segment (511) disposed in the accommodating space (295) and sandwiched in between said moisture detector (22) and said base plate (291), and a second segment (512) extending from said first segment (511) through said positioning wall (292) out of said mounting seat (29) and mounted with said at least one sampling element (52).

2. The wetness notification system as claimed in claim 1, characterized in that said positioning wall (292) is formed with a through hole (293), and said second segment (512) extends through said through hole (293).

3. The wetness notification system as claimed in claim 1, characterized in that said positioning wall (292) is formed with at least one notch (294) depressed toward said base plate (291) and facilitating deformation of said positioning wall (292) for removing said moisture detector (22) from the accommodating space (295).

4. The wetness notification system as claimed in claim 3, characterized in that said second segment (512) extends through said at least one notch (294).

5. The wetness notification system as claimed in claim 1, characterized in that said positioning wall (292) is formed with a plurality of notches (294) depressed toward said base plate (291), and said second segment (512) extends through one of said notches (294).

6. The wetness notification system as claimed in claim 1, characterized in that said sampling unit (5) includes a plurality of said sampling elements (52) disposed on said second segment (512) of said substrate (51).

7. The wetness notification system as claimed in claim 1, characterized in that said sampling unit (5) further includes a protection sleeve (53) that is made of silicone, that covers a distal end of said second segment (512) without covering said at least one sampling element (52), and that has a curved end opposite to said first segment (511).

8. The wetness notification system as claimed in claim 1, characterized in that said positioning wall is
    formed with a through hole (293) and a plurality of notches (294) that are depressed toward said base plate (291) and that facilitate deformation of said positioning wall (292) for removing said moisture detector (22) from the accommodating space (295),
    characterized in that said sampling unit (5) further includes a protection sleeve (53) that is made of silicone, that covers a distal end of said second segment (512) without covering said at least one sampling element (52), and that has a curved end opposite to said first segment (511).

9. The wetness notification system as claimed in claim 1, characterized in that said casing (23) includes an input port (231), and said second end of said transmission wire (28) includes a connector (281) removably inserted into said input port (231).

10. The wetness notification system as claimed in claim 1, further characterized by a positioning member (6) that engages said clip unit (3) and that is formed with a slit (61) for receiving a section of said transmission wire (28) so as to position said transmission wire (28).

* * * * *